(12) United States Patent
Wang et al.

(10) Patent No.: US 8,158,549 B2
(45) Date of Patent: Apr. 17, 2012

(54) CATALYSTS FOR FLUOROOLEFINS HYDROGENATION

(75) Inventors: Haiyou Wang, Amherst, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/554,559

(22) Filed: Sep. 4, 2009

(65) Prior Publication Data

US 2011/0060172 A1   Mar. 10, 2011

(51) Int. Cl.
*B01J 27/06* (2006.01)
*B01J 23/40* (2006.01)
*B01J 23/42* (2006.01)
*B01J 23/44* (2006.01)
*B01J 23/70* (2006.01)
*B01J 23/72* (2006.01)
*B01J 23/74* (2006.01)

(52) U.S. Cl. ........ 502/224; 502/326; 502/330; 502/331; 502/337; 502/338; 502/339

(58) Field of Classification Search ............... 502/224, 502/326, 330, 331, 337–339
See application file for complete search history.

(56) References Cited

U.S. PATENT DOCUMENTS

| 4,048,248 | A | * | 9/1977 | Ryu .................... 585/462 |
| 5,089,454 | A | | 2/1992 | Lerot et al. |
| 5,396,000 | A | | 3/1995 | Nappa |
| 5,446,215 | A | * | 8/1995 | Cook et al. ............. 570/142 |
| 5,532,418 | A | * | 7/1996 | Nakada et al. .......... 570/166 |
| 5,679,875 | A | | 10/1997 | Aoyama et al. |
| 6,093,859 | A | | 7/2000 | Nappa et al. |
| 6,368,997 | B2 | * | 4/2002 | Herron et al. .......... 502/302 |
| 2009/0043136 | A1 | | 2/2009 | Wang et al. |
| 2010/0076231 | A1 | | 3/2010 | Nappa et al. |
| 2010/0191024 | A1 | * | 7/2010 | Uenveren et al. ........ 570/151 |

FOREIGN PATENT DOCUMENTS

| JP | 3543863 | | 4/2004 |
| WO | 93/25507 | * | 12/1993 |
| WO | WO2008054778 | | 5/2008 |

OTHER PUBLICATIONS

I. L. Knunyants et al., Izvestiya Akademii Nauk SSSR, Otdelenie Khimicheskikh Nauk, No. 8, pp. 1412-1418 (1960) DE.

* cited by examiner

*Primary Examiner* — Patricia L Hailey
(74) *Attorney, Agent, or Firm* — Bruce Bradford

(57) ABSTRACT

A support of metal oxyfluoride or metal halide for a metal-based hydrogenation catalyst useful in hydrogenating fluoroolefins is provided.

12 Claims, No Drawings

CATALYSTS FOR FLUOROOLEFINS HYDROGENATION

BACKGROUND

1. Field of Invention

The present invention relates to catalysts for hydrogenating olefins. More particularly, this invention relates to supported catalyst for hydrogenating fluoroolefins.

2. Description of Prior Art

Catalytic hydrogenation of fluoroolefins is frequently used in producing hydrofluorocarbons as useful products and/or intermediates. Various metals, such as Pd, supported on a substrate have long been recognized as highly effective hydrogenation catalysts. These catalysts are particularly effective in gas-phase reactions.

In certain reactions, the effectiveness of these catalysts can be increased by incorporating at least one zero-valent metal onto a supporting substrate. Materials such as alumina, silica, titania, and zirconia, as well as titanium oxide, magnesium oxide, and zirconium oxide are known substrates for certain hydrogenation catalysts. (U.S. Pat. No. 5,089,454). Knunyants et al. (see Izv. Akad. Nauk. SSSR, (1960) 1412-1418) reports a $Pd/Al_2O_3$ catalyst used to catalyze the hydrogenation of $CF_3CF=CF_2$ (HFP) to $CF_3CHFCHF_2$ (236ea), and $CF_3CF=CHF$ (1225ye) to $CF_3CHFCH_2F$ (245eb). However, due to the occurrence of hydrogenolytic cleavage of the carbon-fluorin bond, small amount of HF is generated during reaction, which attacks alumina, silica, titania, and zirconia that are known as the normal carrier of palladium, causing catalyst structure change and catalyst deactivation. Japan Patent JP Patent 3543863 teaches the use of a Pd/carbon catalyst that is resistant to HF attack for the hydrogenation of HFP to 236a. U.S. Pat. No. 5,396,000 teaches the use of a Pd/carbon catalyst for the hydrogenation of 1225ye to 245eb. However, these carbon supported metal catalysts are not regenerable once deactivated. Therefore, there is a need for a new type of catalyst that is not only resistant to HF attack but also regenerable once deactivated for the hydrogenation of fluoroolefins.

SUMMARY OF THE INVENTION

Applicants unexpectedly found that metal catalysts supported on metal oxyfluorides and certain metal fluorides provide stable activity for the hydrogenation of fluoroolefins, while those supported on metal oxides exhibit unstable activity.

Accordingly, in one aspect of the invention provided is an article of manufacture comprising (a) a solid support comprising a metal oxyfluoride or a metal fluoride, wherein said metal fluoride is selected from the group consisting of $CrF_3$, $TiF_4$, and $ZrF_4$; and (b) at least one elemental metal disposed on or within said support, preferably wherein said elemental metal is present in an amount from about 0.05 to about 10 weight percent based upon the total weight of the metal and support. In certain preferred embodiments, the carrier of the catalyst is selected from the group consisting of oxyfluorides of Al, Cr, Ti, Zr, Mg, etc., or metal fluorides selected from the group consisting of $CrF_3$, $TiF_4$, and $ZrF_4$. Non-limiting examples of elemental metals include Pd, Ru, Pt, Rh, Ir, Fe, Co, Ni, Cu, Ag, Re, Os, Au, and any combinations thereof.

According to another aspect of the invention, provided is a method for preparing a catalyst comprising (a) contacting at least one metal salt, at least one solvent, and a metal fluoride or metal oxyfluoride to form a slurry; (b) removing said solvent from said slurry to form a solvent-free powder; (c) optionally calcining said powder; (d) transforming said powder into a supported catalyst; and (e) contacting said support catalyst with a gaseous composition comprising $H_2$ to activate said supported catalyst, wherein said activated supported catalyst comprises about 90 to about 99.95 weight percent of metal fluoride or metal oxyfluoride and about 0.05 to about 10 weight percent of a zero-valent metal derived from said metal salt. In a preferred embodiment, the method comprising the steps of (a) dissolving a salt of metal component (e.g., $Pd(NO_3)_2$, $PdCl_2$ for Pd) in a suitable solvent to form a solution; (b) adding a suitable amount of metal oxyfluoride or metal fluoride into said solution to form a slurry; (c) driving off the solvent from said slurry to form a paste; (d) drying said paste to form solvent-free powder; (e) calcining said solvent-free powder in $N_2$ flow for 2 to 8 hours at 300-500° C.; (f) grinding the calcined powder to a finely divided state; (g) palletizing said fine powder into tablets; and (h) reducing said catalyst pellets in $H_2$ or diluted $H_2$ flow for 2 to 4 hours at 150-250° C. prior to use.

According to yet another aspect of the invention, provided is a method for hydrogenating a compound comprising contacting a reactant comprising an olefin having at least one carbon-fluorine bond with a supported hydrogenation catalyst under reaction conditions effective to form a reaction product comprising a hydrogenated derivative of said olefin, wherein said supported hydrogenation catalyst comprises (a) an elemental metal selected from Pd, Ru, Pt, Rh, Ir, Fe, Co, Ni, Cu, Ag, Re, Os, Au, and any combinations thereof; and (b) a support comprising at least about 75 wt. % of a metal fluoride selected from the group consisting of $CrF_3$, $TiF_4$, and $ZrF_4$, or a metal oxyfluoride selected from the group consisting of magnesium (II) oxyfluoride, aluminum (III) oxyfluoride, chromium (III) oxyfluoride, titanium (IV) oxyfluoride, and zirconium (IV) oxyfluoride. A preferred embodiment of this method comprises the steps of (a) adding hydrogen and a fluoroolefin to a reaction vessel containing a hydrogenation catalyst; and (b) reacting said fluoroolefin with hydrogen over said hydrogenation catalyst to produce a hydrofluorocarbon. Non-limiting examples of hydrofluorocarbons that can be produced through the hydrogenation of certain fluoroolefins include 1,1,1,2,3,3-hexafluoropropane (236ea), 1,1,1,2,3-pentafluoropropane (245eb), 1,1,1,3,3-pentafluoropropane (245fa), 1,1,1,3-tetrafluoropropane (254fa), and 1,1,1,2-tetrafluoropropane (254eb).

DETAILED DESCRIPTION OF PREFERRED EMBODIMENTS OF THE INVENTION

According to a preferred embodiment of the invention, selected supported metal catalysts are employed in the hydrogenation of fluoroolefins to hydrofluorocarbons. Non-limiting examples of metal components include Pd, Ru, Pt, Rh, Ir, Fe, Co, Ni, Cu, Ag, Re, Os, Au, etc. The metal loading can varied within a large range, e.g., from 0.05-10 wt %. However, for noble metals such as Ru, Ph, Pd, Pt, Ir, etc., the metal loading is preferably lower than 5 wt %, and more preferably lower than 1 wt %. There are two classes of catalyst supports useful in the present invention: (i) metal oxyfluorides, and (ii) metal fluorides selected from $CrF_3$, $TiF_4$, and $ZrF_4$.

In certain preferred embodiments, the catalyst support is the oxyfluorides of metals, preferably bi-, tri-, and tetravalent metals, more preferably tri-, and tetra-valent metals, and most preferably tri-valent metals. Component metals include, but are not limited to, $Mg^{2+}$, $Al^{3+}$, $Cr^{3+}$, $Ti^{4+}$, and $Zr^{4+}$. In one embodiment, metal oxyfluorides are prepared through fluorinating corresponding metal oxides with HF for a long enough time at a temperature higher than the reaction temperature of fluoroolefin hydrogenation. The fluorine content in metal oxyfluoride is hence mainly determined by the temperature adopted in fluorination process. No further reaction takes place between such prepared metal oxyfluoride and HF during the catalytic hydrogenation of fluoroolefins.

In certain preferred embodiments, the catalyst supports are the fluorides of metals, preferably bi-, tri-, and tetra-valent metals, more preferably tri- and tetra-valent metals, and most preferably tri-valent metals. Component metals include $Cr^{3+}$, $Ti^{4+}$, and $Zr^{4+}$. In one embodiment, metal fluorides are prepared by reacting metal hydroxide with hydrofluoric acid. Since the metal is fully fluorinated, no reaction between metal fluoride support and HF generated as by-product is expected during the hydrogenation of fluoroolefins.

In certain embodiments, the catalyst of the present invention is prepared by adding the salt of a metal catalyst component (e.g., $Pd(NO_3)_2$ or $PdCl_2$ for Pd) to an amount of solvent sufficient to substantially dissolve or solubilize the metal salt. The preferred solvent is one in which the metal salt is readily soluble. The choice of solvent may vary depending on the particular metal salts. Examples of solvents that can be used for the preparation of the catalyst compositions of the present invention include water, alcohols, ethers, and mixtures thereof. Useful alcohols include monohydric and polyhydric alcohols. Most preferred alcohols are those that are monohydric and have 1 to 5 carbon atoms. A most preferred solvent is water.

A metal oxyfluoride (e.g., $AlO_xF_y$) or metal fluoride (e.g., $AlF_3$) is then added to the solution of said metal salt to form a slurry. After formation of the slurry, substantially all of the solvent is removed to form a solid mass of a mixture of said metal salt and said metal oxyfluoride (or metal fluoride). Although the solvent can be removed in one step, a preferred method is to drive off a portion of the solvent from the slurry to form a paste and then followed by drying the paste to form the solid mass. Any conventional technique can be used to drive off the solvent. Examples of such techniques include vigorous stirring at room or elevated temperatures, evaporation, settling and decanting, centrifugation, and filtration. It is preferred to evaporate off a desired amount of solvent to form the paste. The paste is then dried by any suitable method to form a free-flowing, substantially solvent-free powder. Preferred methods for drying include oven drying, most preferably at temperatures from about 110° C. to about 120° C., and spray drying. Being solvent free means that less than 1 wt. %, preferably about 0.5 wt % or less, more preferably about 0.1 wt % or less, and most preferably no solvent will remain with the powder after solvent removal/drying. Upon removal of solvent, the powder will take the form of a solid mass (or powder) of a mixture of particles of said metal salt and said metal oxyfluoride (or metal fluoride).

Optionally, the solid mass of the mixture of said metal salt and said metal oxyfluoride (or metal fluoride) powder is then calcined. Calcination is preferably carried out at a temperature of about 100° C. to about 750° C., more preferably at a temperature of about 200° C. to about 600° C., and most preferably at a temperature of about 300° C. to about 500° C. Calcination may further optionally be carried out in the presence of an inert gas, such as nitrogen or argon.

After calcination, the powder is optionally further grinded such that it becomes more finely-divided. The powder is further optionally pelletized in order to form pellets.

The catalyst pellets are then loaded into a reactor and prior to use are reduced in hydrogen or diluted hydrogen flow for 2-4 hours at a temperature of about 50 to about 500° C., more preferably at a temperature of about 100 to about 300° C., and most preferably at a temperature of about 150 to about 250° C.

It may also be advantageous to periodically regenerate the catalyst after prolonged use while in place in the reactor. Regeneration of the catalyst may be accomplished by any means known in the art. One method is by passing oxygen or oxygen diluted with nitrogen over the catalyst at temperatures of about 200° C. to about 600° C. (preferably about 350° C. to about 450° C.) for about 0.5 hour to about 3 days followed by reduction treatment in hydrogen or diluted hydrogen flow for 2-4 hours at a temperatures of about 50° C. to about 500° C. (preferably about 100° C. to about 300° C.).

Although it is contemplated that the hydrogenation of fluoroolefins may be conducted in batch operation, it is preferred that the hydrogenation reaction is carried out as a substantially continuous operation. Furthermore, while it is possible that the hydrogenation reaction may involve in certain embodiments a liquid phase reaction, it is contemplated that in preferred embodiments the hydrogenation reaction comprises, and even more preferably consists of, at least two vapor phase reaction stages.

With respect to the number of reaction stages, applicants have found surprisingly and unexpectedly found that overall reaction conversion and selectivity can be achieved at relatively high levels by the use of at least two reaction stages wherein the first stage of reaction is conducted under conditions effective to achieve a first, relatively low rate of conversion to produce a first stage reaction effluent, and at least a second stage of reaction which is fed by at least a portion of said first stage effluent and which is conducted under conditions effective to achieve a second rate of conversion higher than said first rate. Preferably, reaction conditions are controlled in each of the first and second stages in order to achieve the desired conversion in accordance with the present invention. As used herein, the term "reaction conditions" is intended to include the singular and means control of any one or more processing parameters which can be modified by the operator of the reaction to produce the conversion of the feed material in accordance with the teachings contained herein. By way of example, but not by way of limitation, conversion of the feed material may be controlled or regulated by controlling or regulating any one or more of the following: the temperature of the reaction, the flow rate of the reactants, the presence of diluent, the amount of catalyst present in the reaction vessel, the shape and size of the reaction vessel, the pressure of the reaction, and any one combinations of these and other process parameters which will be available and known to those skilled in the art in view of the disclosure contained herein.

Applicants have found that in preferred embodiments the step of controlling the conversion in the first stage of the hydrogenation reaction is achieved by judicious selection and control of the amount of catalyst present in the first stage of reaction relative to the feed rate of one or more of the reactants and/or by judicious selection and control of the reaction temperature, and preferably by judicious selection and control of both of these process parameters. The step of judiciously selecting the amount of catalyst to be used in the first stage of reaction includes the step of estimating the amount of catalyst theoretically needed to convert 100% of the feed material. Such an estimate can be obtained by any and all known methods for making such an estimate, which should be apparent to those skilled in the art in view of the teachings contained herein. In addition, the step of judiciously selecting the amount of catalyst may also involve conducting bench, pilot or similar studies to determine the amount of the particular catalyst being used which is needed to convert 100% of the feed material under the feed rate in other process parameters which have otherwise been chosen. Based upon this estimate, the preferred embodiments of the present invention then include the step of providing in the first stage of reaction an amount of catalyst that is substantially below the amount required for 100% conversion, and even more preferably is sufficiently low so as to result in a conversion of the feed olefin of from about 10% to about 60%, more preferably from about 10% to about 40%, and even more preferably from about 10% to 25%. Once again, those skilled in the art will appreciate that the step of judiciously choosing the amount of catalyst may further include running additional bench, pilot or other studies with the reduced amount of catalyst and adjusting the amount of catalyst accordingly. It is contemplated that all such studies and estimates can be achieved without undue experimentation in view of the teachings contained herein.

Applicants have found that the step of maintaining a relatively low conversion of reactant in accordance with the present invention in a first stage of reaction has an advantageous affect on the selectivity of the reaction to the desired hydrofluorocarbon. In other words, although the amount of conversion which occurs in the first stage of reaction is controlled to be well below that which is desired for the overall hydrogenation step, applicants have found that an improved, higher percentage of the feed material is converted to the desired hydrofluorocarbon in the first reaction stage (that is, improved selectivity is achieved) by controlling the conversion as described herein. More specifically, is preferred in many embodiments that the selectivity to the desired hydrofluorocarbon in the first reaction stage is at least about 80%, more preferably at least about 90%, and even more preferably at least about 95%, and in many preferred embodiments about 97% or greater.

In certain preferred embodiments the step of controlling the conversion in the first reaction stage further includes removing heat from the reaction by cooling at least a portion of the reaction mixture. It is contemplated that those skilled in the art will be able to devise without undue experimentation and many means and mechanisms for attaining such cooling in view of the teachings contained herein and all such means and mechanisms are with the scope of the present invention.

In preferred embodiments, at least a portion of the effluent from the first reaction stage is fed directly, or optionally after some further processing, to a second reaction stage in which the unreacted fluoroolefin remaining in the effluent after the first reaction stage is converted to the hydrofluorocarbon in accordance with the present invention. More specifically is preferred that the second reaction stage or subsequent reaction stages if present, is operated under conditions effective to convert the fluoroolefin contained in the feed stream to the second reactor stage at a conversion rate that is greater than, and preferably substantially greater than, the conversion percentage in the first reaction stage. In certain preferred embodiments, for example, the conversion percentage in the second reaction stage is from about 20% to about 99%, depending in large part upon the total number of reactant stages used to affect the overall conversion step. For example, in embodiments consisting of a two-stage reaction system, it is contemplated that the conversion in the second reaction stage is preferably greater than 95%, and even more preferably about 100%. However, as those skilled in the art will appreciate from the teachings contained herein, such a two-stage reaction may not be sufficient to produce the desired selectivity to the hydrofluorocarbon. In such cases, it is within the scope of the present invention that the conversion step may comprise greater than two reaction stages, including in some embodiments as many 10 or more reaction stages.

The size and shape, and other characteristics of the reaction vessel itself may vary widely with the scope of the present invention, and it is contemplated that the vessel associated with each stage may be different than or the same as the vessel associated with the upstream and downstream reaction stages. Furthermore, it is contemplated that all reaction stages can occur inside a single vessel, provided that means and mechanisms necessary to control conversion are provided. For example, it may be desirable in certain embodiments to utilize a single tubular reactor for each reaction stage, providing conversion control by judicious selection of the amount and/or distribution of catalyst throughout the tubular reactor. In such a case, it is possible to further control the conversion in different sections of the same tubular reactor by controlling the amount of heat removed from or added to different sections of the tubular reactor.

The catalyst compositions disclosed in the present invention are useful in converting fluoroolefins to hydrofluorocarbons. One or more of the hydrogenation catalyst disclosed in the present invention may be used for one or more of the reaction stages in accordance with the present invention. In certain preferred embodiments, the catalyst preferably comprises palladium supported on aluminum oxyfluoride.

Thus, certain embodiments of the present methods comprise bringing a fluoroolefin and a hydrogenation agent, such as $H_2$, into contact with a first amount of catalyst in a first reaction stage to produce a reaction stream comprising hydrofluorocarbon(s), unreacted fluoroolefin and hydrogen; contacting at least a portion of this first effluent stream with a second amount of catalyst in a second stage of reaction to produce a hydrofluorocarbon, wherein the second amount of catalyst is greater than the first amount of catalyst and wherein conversion to the fluoroolefin is higher in the second stage of reaction.

Table 1 sets forth examples of hydrofluorocarbons and fluoroolefins from which they can be obtained (fluoroolefin in left column and corresponding hydrofluorocarbon in the right column).

TABLE 1

| Fluoroolefins | Hydrofluorocarbons |
| --- | --- |
| 1,1,2,3,3,3-hexafluoropropene $CF_3CF=CF_2$ (1216) | 1,1,1,2,3,3-hexafluoropropane $CF_3CHFCHF_2$ (236ea) |
| 1,2,3,3,3-pentafluoropropene $CF_3CF=CHF$ (Z/E-1225ye) | 1,1,1,2,3-pentafluoropropane $CF_3CHFCH_2F$ (245eb) |
| 1,1,3,3,3-pentafluoropropene $CF_3CH=CF_2$ (1225zc) | 1,1,1,3,3-pentafluoropropane $CF_3CH_2CHF_2$ (245fa) |
| 1,3,3,3-tetrafluoropropene $CF_3CH=CHF$ (trans/cis-1234ze) | 1,1,1,3-tetrafluoropropane $CF_3CH_2CH_2F$ (254fb) |
| 2,3,3,3-tetrafluoropropene $CF_3CF=CH_2$ (1234yf) | 1,1,1,2-tetrafluoropropane $CF_3CHFCH_3$ (254eb) |

EXAMPLE

The following is example of the invention and is not to be construed as limiting.

Example 1

Hydrogenation of 1,1,1,2,3,3-hexafluoropropene over a fluorinated metal oxide and metal fluoride supported Pd catalysts In example 1, three supported Pd catalysts are compared for conversion efficiency in the hydrogenation of 1,1,1,2,3,3-hexafluoropropene (HFP). More particularly, a 1 wt % $Pd/AlO_xF_y$, according to the present invention was compared to a 1 wt % $Pd/AlF_3$ and a 1 wt % $Pd/MgF_2$. 2 g of catalyst diluted with 20 ml of Monel packing was charged into a ¾" Monel tube reactor and was in-situ reduced in 10% $H_2/N_2$ flow for 2 hours at 200° C. HFP was fed into reactor at a rate of 10 g/h, and $H_2$ was co-fed according to a mole ratio of $H_2$/HFP equal to 1.5. As shown in Table 2, the 1 wt % $Pd/AlO_xF_y$ catalyst provided an HFP conversion of around 98% and a 236ea selectivity of about 99% at 100° C., the 1% $Pd/AlF_3$ catalyst exhibited an HFP conversion of around 80% and a 236ea selectivity of about 99.5% at 100° C., and the 1% $Pd/MgF_2$ one showed an activity close to 40% and a 236ea selectivity of about 97% at 150° C., indicating all three catalysts are highly selective to form 236ea.

TABLE 2

| | | HFP hydrogenation over metal fluoride supported Pd catalysts | | | |
|---|---|---|---|---|---|
| Catalyst | Temp. (° C.) | Conversion, % HFP | Selectivity, % 236ea | Selectivity, % 245eb | Selectivity, % others |
| 1% Pd/AlO$_x$F$_y$* | 100 | 97.6 | 98.9 | 0.6 | 0.5 |
| 1% Pd/AlF$_3$ | 100 | 80.4 | 99.6 | 0.4 | 0.0 |
| 1% Pd/MgF$_2$ | 150 | 38.6 | 97.0 | 1.5 | 1.5 |

*The AlO$_x$F$_y$ support was obtained through the fluorination of Al$_2$O$_3$ in 5.4% HF/N$_2$ flow for 2 hours at 400° C.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claim.

What is claimed is:

1. An article of manufacture comprising:
   a. a solid support comprising a metal oxyfluoride or a metal fluoride, wherein said metal fluoride is selected from the group consisting of CrF$_3$, TiF$_4$, and ZrF$_4$; and
   b. at least one elemental metal disposed on or within said support, wherein a total amount of all of the elemental metal(s) disposed on or within said support is less than 1 weight percent, based upon the total weight of the elemental metal and support.

2. The article of claim 1 wherein said solid support comprises a metal oxyfluoride and said elemental metal is one or more reduced zero-valent metals.

3. The article of claim 2 wherein said metal oxyfluoride is selected from the group consisting of magnesium (II) oxyfluoride, aluminum (III) oxyfluoride, chromium (III) oxyfluoride, titanium (IV) oxyfluoride, and zirconium (IV) oxyfluoride.

4. The article of claim 2 wherein said support comprises at least about 75 wt. % of said metal oxyfluoride.

5. The article of claim 2 wherein said support consists essentially of said metal oxyfluoride.

6. The article of claim 2 wherein said elemental metal is selected from the group consisting of Pd, Ru, Pt, Rh, Ir, Fe, Co, Ni, Cu, Ag, Re, Os, Au, and any combinations thereof.

7. The article of claim 1 wherein the total amount of the elemental metal comprises about 0.05 to less than 1 weight percent of the combined weight of said metal and said support.

8. The article of claim 1 wherein said solid support comprises said metal fluoride and said elemental metal is one or more reduced zero-valent metals.

9. The article of claim 8 wherein said support comprises at least about 75 wt. % of said metal fluoride.

10. The article of claim 8 wherein said support consists essentially of said metal fluoride.

11. The article of claim 8 wherein said elemental metal is selected from the group consisting of Pd, Ru, Pt, Rh, Ir, Fe, Co, Ni, Cu, Ag, Re, Os, Au, and any combinations thereof.

12. The article of claim 8 wherein the total amount of the elemental metal comprises about 0.05 to less than 1 weight percent of the combined weight of said metal and said support.

* * * * *